United States Patent
Déhais et al.

(10) Patent No.: US 9,976,092 B2
(45) Date of Patent: May 22, 2018

(54) DETERMINING MODIFIED TAN-IR IN CRUDE OIL

(71) Applicant: FINA TECHNOLOGY, INC., Houston, TX (US)

(72) Inventors: Fabrice Déhais, Houston, TX (US); Xavier Roumeau, Beaumont, TX (US); Jun Wang, Houston, TX (US); Ryan Jones, Rosharon, TX (US); Kevin Kelly, Friendswood, TX (US)

(73) Assignee: Fina Technology, Inc., Houston, TX (US)

( * ) Notice: Subject to any disclaimer, the term of this patent is extended or adjusted under 35 U.S.C. 154(b) by 43 days.

(21) Appl. No.: 14/927,618

(22) Filed: Oct. 30, 2015

(65) Prior Publication Data

US 2016/0145498 A1 May 26, 2016

Related U.S. Application Data

(60) Provisional application No. 62/083,711, filed on Nov. 24, 2014.

(51) Int. Cl.

| | |
|---|---|
| *C10G 19/073* | (2006.01) |
| *C10G 25/00* | (2006.01) |
| *C10G 29/16* | (2006.01) |
| *G01N 21/3577* | (2014.01) |
| *C10G 7/10* | (2006.01) |
| *C10G 7/00* | (2006.01) |
| *C10G 7/06* | (2006.01) |
| *G01N 33/28* | (2006.01) |
| *C10G 19/02* | (2006.01) |
| *G01N 21/35* | (2014.01) |

(52) U.S. Cl.
CPC ............... *C10G 7/10* (2013.01); *C10G 7/00* (2013.01); *C10G 7/06* (2013.01); *C10G 19/02* (2013.01); *G01N 21/3577* (2013.01); *G01N 33/2823* (2013.01); *C10G 2300/203* (2013.01); *G01N 2021/3595* (2013.01)

(58) Field of Classification Search
CPC ...... C10G 19/073; C10G 25/00; C10G 29/16; C10G 2300/203; G01N 21/3577
See application file for complete search history.

(56) References Cited

U.S. PATENT DOCUMENTS

| | | | |
|---|---|---|---|
| 6,022,494 A * | 2/2000 | Sartori | C10G 19/00 208/47 |
| 6,258,258 B1 | 7/2001 | Sartori et al. | |
| 6,544,411 B2 | 4/2003 | Varadaraj | |
| 7,160,728 B2 | 1/2007 | Chimenti et al. | |
| 2002/0006667 A1* | 1/2002 | Chimenti | G01N 33/2876 436/60 |
| 2004/0106204 A1 | 6/2004 | Chimenti et al. | |
| 2009/0294672 A1 | 12/2009 | Da Silva et al. | |
| 2012/0160709 A1 | 6/2012 | Kusinski et al. | |

OTHER PUBLICATIONS

A. Zhang et al., Naphthenic Acid Removal From Crude Oil Through Catalytic Decarboxylation on Magnesium Oxide, 303 Appl. Catal., A 103-109 (2006).*
International Search Report and Written Opinion issued in Application No. PCT/US2015/058212, dated Jan. 21, 2016, 9 pages.
Brian Benoit, et al., "Overcoming the Challenges of Tight/Shale Oil Refining", Processing Shale Feedstocks 2014; www.eptq.com; pp. 37-44.
Frederick van de Voort, et al., "Quantitative FTIR Condition Monitoring—Analytical Wave of the Future?"; 2001.

\* cited by examiner

*Primary Examiner* — Randy Boyer
(74) *Attorney, Agent, or Firm* — Albert Shung

(57) ABSTRACT

A method for determining a TAN-IR for naphthenic acids in crude oil or crude oil fraction may include determining an IR spectrum of a sample of the crude oil or crude oil fraction. The method may include determining an IR spectrum of a neutralized sample of the crude oil or crude oil fraction. The method may include utilizing the IR spectra of the sample and the neutralized sample to determine a modified TAN-IR.

18 Claims, 1 Drawing Sheet

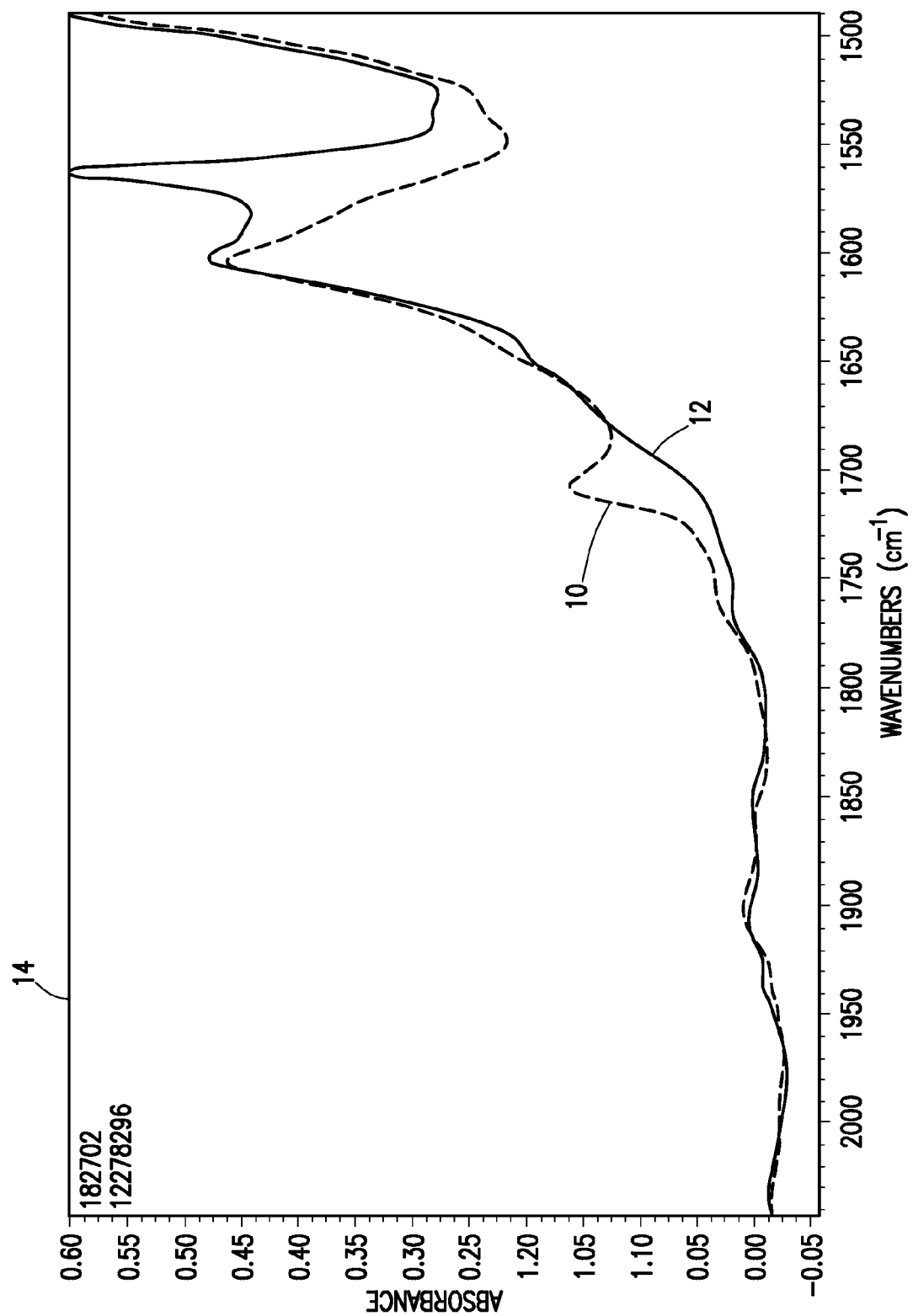

DETERMINING MODIFIED TAN-IR IN CRUDE OIL

CROSS-REFERENCE TO RELATED APPLICATIONS

The present application claims priority from U.S. Provisional Patent Application No. 62/083,711, filed on Nov. 24, 2014, the entirety of which is incorporated herein by reference.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Technical Field

This disclosure generally relates to determining modified TAN-IR in crude oil, crude oil fractions, and crude oil blends, and to crude oil, crude oil fractions, and crude oil blends formed based upon the determined modified TAN-IR.

Background

Processing of crude oil or crude oil fractions having high total acid numbers (TAN) can provide increased feedstock valorization in comparison to processing with purely conventional crude oils. The refining of crude oil that has a high TAN can have undesirable effects, such as causing corrosion of processing equipment in contact with the crude oil or crude oil fraction. Certain acids in crude oil can cause more corrosion than other acids that may be found in crude oil. Determining a level of certain acids in crude oil can allow the level of these acids in crude oil to be maintained at or below a predetermined level. It can be desirable to blend crude oil that contains acids with other sources of crude oil or fractions of crude oil, while maintaining the level of certain acids in the blend at or below a predetermined level.

SUMMARY

An embodiment of the present disclosure includes a method for determining a modified TAN-IR of a crude oil or crude oil fraction. The method includes obtaining a first sample and a second sample of the crude oil or crude oil fraction that contains naphthenic acid. The method includes determining an IR spectrum of the first sample. The method includes contacting the second sample with a metallic hydroxide to form a neutralized sample, and determining an IR spectrum of the neutralized sample. The method includes subtracting the IR spectrum of the neutralized sample from IR spectrum of the first sample to determine a modified TAN-IR.

Another embodiment of the present disclosure includes a method for determining a modified TAN-IR of a crude oil or crude oil fraction. The method includes determining a modified TAN-IR by subtracting an IR spectrum of a neutralized sample from an IR spectrum of a first sample. The first sample is a portion of a crude oil or crude oil fraction that contains naphthenic acid. The neutralized sample is a portion of the crude oil or crude oil fraction after contact with a metallic hydroxide.

Another embodiment of the present disclosure includes a method for determining a modified TAN-IR of a crude oil or crude oil fraction. The method includes obtaining a sample of a crude oil or crude oil fraction that contains naphthenic acid, and determining an IR spectrum of the sample. The method includes contacting the sample with a metallic hydroxide to form a neutralized sample, and determining an IR spectrum of the neutralized sample. The method includes subtracting the IR spectrum of the neutralized sample from the IR spectrum of the sample to determine a modified TAN-IR.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

FIGURE depicts a graph with an IR spectrum of an oil sample and an IR spectrum of a neutralized oil sample consistent with at least one embodiment of the present disclosure.

DETAILED DESCRIPTION

A detailed description will now be provided. The description includes specific embodiments, versions and examples, but the disclosure is not limited to these embodiments, versions or examples, which are included to enable a person having ordinary skill in the art to make and use the disclosure when that information is combined with available information and technology.

Various terms as used herein are shown below. To the extent a term used in a claim is not defined below, it should be given the broadest definition skilled persons in the pertinent art have given that term as reflected in printed publications and issued patents at the time of filing. Further, unless otherwise specified, all compounds described herein may be substituted or unsubstituted and the listing of compounds includes derivatives thereof.

Refining crude oil containing acids, such as crude oils that have a high Total Acid Number (TAN), may allow refineries to increase valorization compared to conventional crudes. Crude oil with high TAN may impose potential challenges to process units, such as high temperature corrosion by naphthenic acids.

TAN in crude oil may be measured using ASTM method D664, Standard Test Method for Acid Number of Petroleum Products by Potentiometric Titration. ASTM method D664 may capture all acidic species present in a sample, including inorganic, organic, noncorrosive and corrosive acidic species. Use of ASTM method D664 may lead to an overestimation of the TAN composition and corrosion potential, resulting in a reduction in processing throughput of high margin opportunity crudes.

Fourier Transfer Infrared Spectroscopy (FTIR) based TAN analysis (TAN-IR) may be used to quantify an acid portion of a sample of crude oil that may be most damaging during crude oil processing, such as naphthenic acids.

Naphthenic acids are characterized by the presence of one or more carboxylic acid groups. Naphthenic acids may include cyclopentyl and cyclohexyl carboxylic acids with molecular weights ranging from about 120 to over 700 atomic mass units. Naphthenic acids may cause naphthenic acid corrosion on processing equipment, such as distillation units. The ability to determine the concentration of naphthenic acids in crude oil or crude oil fractions may allow for the assessment of high temperature corrosion constraints while optimizing incorporation of crude oil containing naphthenic acids into distillation units or other downstream processing units.

One or more embodiments include a method for determining a modified TAN-IR acid number in crude oil or crude oil fraction. As used herein, modified TAN-IR refers to TAN-IR utilized to determine an acid number for naphthenic acid, as opposed to direct TAN-IR utilized to determine the Total Acid Number. Direct TAN-IR used to determine the Total Acid Number, may include interferences due to other non-naphthenic acid species. Because these interferences may lead to an overestimation of the TAN-IR when measured directly, determining the modified TAN-IR may allow a more accurate determination of a concentration of naphthenic acid in crude oil or crude oil fraction than use of direct TAN-IR.

The method may include obtaining a first sample and a second sample of a crude oil or crude oil fraction that contains naphthenic acid. In one or more embodiments, the crude oil or crude oil fraction may include atmospheric gas oil (AGO), furnace oil (FO), atmospheric tower bottom (ATB), light vacuum gas oil (LVGO), or heavy vacuum gas oil (HVGO).

The method may include determining an IR spectrum of the first sample. The IR spectrum of the first sample may be determined using an FTIR spectrometer. Non-limiting examples of FTIR spectrometers include mid-infrared FTIR, or a Thermo Nicolet 670 infrared spectrometer, available from Thermo Scientific of Waltham, Mass., US. In one or more embodiments, the FTIR spectrometer used to determine each IR spectrum disclosed herein may include one or more flip top cells, such a model Alpha Q410 FTIR, available from Spectro Scientific of Chelmsford, Mass., US.

In one or more embodiments, each IR spectrum determined in the method may be taken within a wavelength range of from about 1,500 to about 2,500 $cm^{-1}$, or from about 1,650 to about 1,750 $cm^{-1}$, or from about 1,679.70 to about 1,730.69 $cm^{-1}$.

The method may include contacting the second sample with a metallic hxdroxide, including, but not limited to, magnesium hydroxide (MgOH), sodium hydroxide (NaOH), or potassium hydroxide (KOH), to form a neutralized sample. For example, the second sample may be contacted with an amount of metallic hydroxide sufficient to neutralize the naphthenic acid in the crude oil or crude oil fraction.

The method may include determining an IR spectrum of the neutralized sample. The IR spectrum of the neutralized sample may be determined using an FTIR spectrometer in the same manner as the first sample.

In one or more embodiments, rather than utilizing a first sample of the crude oil or crude oil fraction and a second sample of the crude oil or crude oil fraction, the method may include utilizing the same crude oil or crude oil fraction sample to form an IR spectrum of the crude oil or crude oil fraction, and an IR spectrum of the sample after contact with metallic hydroxide. For example, the method may include obtaining a first sample of a crude oil or crude oil fraction that contains naphthenic acid. The method may include determining an IR spectrum of the first sample, in the same manner as discussed above. After determining the IR spectrum of the first sample, the method may then include contacting the first sample with a metallic hydroxide to form a neutralized sample. The method may include determining an IR spectrum of the neutralized sample, in the same manner as discussed above.

In one or more embodiments, the first sample, the neutralized sample, or both may be subjected to sonication, optionally while being heated prior to analysis in the FTIR spectrometer. For example, if the crude oil or crude oil fraction has a low viscosity, the samples can be mixed, such as through sonication, optionally while being heated. The sonication may be performed in a sonicator. The sonication may be performed for a time period ranging from about 1 minute to about 1 hour, about 15 minutes to about 45 minutes, about 25 minutes to about 35 minutes, or about 30 minutes. The heating may be performed in a water bath, for example. The heating may be performed at a temperature ranging from about 20° C. to about 70° C., or about 30° C. to about 60° C., or about 40° C. to about 50° C.

In one or more embodiments, the first sample, the neutralized sample, or both may be subjected to heating and stirring prior to analysis in the FTIR spectrometer. For example, if the crude oil or crude oil fraction is solid or has a high viscosity, the crude oil or crude oil fraction may be subjected to heating and stirring. The heating may be performed on a hot plate. In one or more embodiments, the samples may be stirred while being heated on the hot plate, such as with a magnetic stirrer. The heating may be performed at a temperature ranging from about 100° C. to about 160° C., or from about 110° C. to about 150° C., or from about 120° C. to about 140° C., or at about 130° C. The sample may be subjected to heating and stirring for a time period ranging from about 5 to 35 minutes, or about 10 to 25 minutes, or about 15 to 20 minutes.

The method may include utilizing the IR spectrum of the neutralized sample and the IR spectrum of the first sample to determine the modified TAN-IR. In some embodiments, the method includes subtracting the IR spectrum of the neutralized sample and the IR spectrum of the first sample to determine the modified TAN-IR. The modified TAN-IR may be correlated with a concentration of naphthenic acid in the crude oil or crude oil fraction. For example and without limitation, the IR spectrum of the neutralized sample may be subtracted from the IR spectrum of the first sample. The concentration of naphthenic acids present in the first sample prior to neutralization may be determined from the area under the curve resulting from subtraction of the IR spectrum of the neutralized sample from the IR spectrum of the first sample.

In one or more embodiments, the crude oil or crude oil fraction may be blended with additional crude oil or crude oil fraction to form a blend. The formation of the blend may occur after determination of the modified TAN-IR in the crude oil or crude oil fraction.

In one or more embodiments, the amounts of the crude oil or crude oil fraction and additional crude oil or crude oil fraction in the blend may be maintained such that a modified TAN-IR of the blend is at or below a predetermined level. The predetermined level may be any level of modified TAN-IR. For example, the predetermined level may be a level of modified TAN-IR that processing equipment may tolerate without being subjected to undesirable levels of corrosion. The method may allow an amount of crude oil containing naphthenic acids in the blend to be maximized. In one or more embodiments, the predetermined level of the modified TAN-IR may be 1.5 mg metallic hydroxide/g (e.g., 1.5 mg KOH/g), which may avoid high temperature corrosion. In one or more embodiments, the predetermined level of the modified TAN-IR may be greater than 0.3 mg metallic hydroxide/g (e.g., 0.3 mg KOH/g). In one or more embodiments, the predetermined level of the modified TAN-IR may range from 1.0 to 2.0 mg metallic hydroxide/g (e.g., 1.0 to 2.0 mg KOH/g).

In one or more embodiments, the crude oil or the blend may be fed to a distillation unit. For example, the distillation unit may be an atmospheric distillation unit or a vacuum distillation unit.

The method may include evaluating a risk of corrosion in processing equipment, such as distillation units. The evaluation of the risk of corrosion may include evaluation of various parameters, including operating conditions and materials construction. The operating conditions may include fluid velocity, fluid state, and temperature. The materials of construction may include the metallurgy of circuits. The parameters may be evaluated in relation with the modified TAN-IR and a sulphur content of the crude oil, crude oil fraction, or blend.

For example, in one or more embodiments, a corrosion risk matrix, which may be a software spreadsheet based tool, may be used to calculate an estimation of a corrosion rate. The estimation of the corrosion rate, in conjunction with API-581, may facilitate a corrosion risk assessment. For example, three risk levels may be defined, depending on the estimation of the corrosion rate and the metallurgy of the processing unit(s).

In one or more embodiments, the method may be automated. For example, the collection of IR spectrum and the determination of the modified TAN-IR may be automated. In one or more embodiments, the automated method may allow for the use of the determined modified TAN-IR in real-time, such as to determine a disposition of the crude oil or crude oil fraction. For example, the determined modified TAN-IR may be used, in real-time, to determine a formulation of a blend of the crude oil or crude oil fraction with additional crude oil or crude oil fraction. The determined modified TAN-IR may be used, in real-time, to ensure that the blend has a modified TAN-IR that is at or below a predetermined level.

In one or more embodiments, the automated method may allow for the use of the determined modified TAN-IR to determine adjustments to a formulation of a blend of crude oil, crude oil fraction, or combinations thereof. For example, a modified TAN-IR for a blend may be determined while the blend is being fed to a processing unit, such as a distillation unit. If the modified TAN-IR of the blend is determined to be above a predetermined level, the formulation of the blend may be adjusted to provide the blend with a modified TAN-IR that is at or below the predetermined level. For example, volumetric or weight proportions of constituent crude oil(s) or crude oil fraction(s) in the blend may be adjusted to provide the blend with a modified TAN-IR that is at or below the predetermined level. During adjustment of the blend to provide the blend with a modified TAN-IR that is at or below the predetermined level, the method may include continuing to feed the blend to the processing unit.

EXAMPLES

The disclosure having been generally described, the following examples show particular embodiments of the disclosure. It is understood that the example is given by way of illustration and is not intended to limit the specification or the claims. All compositions percentages given in the examples are by weight.

Example

In this example, about 1.00 gram of oil was placed into a 20 mL disposable scintillation vial to form an oil sample.

To form a neutralized sample, one pellet, weighing from about 0.5 to 1 gram, of KOH was ground into a fine powder with an agate mortar and pestle. The KOH pellets were 99.99% metal basis, semiconductor grade pellets. From 5 to 10 mg of the KOH powder was added to a vial containing 1.00 gram of the oil.

For low viscosity samples of oil, such as AGO or crude oil, the vial of oil may be placed into a sonicator for about 30 minutes with a heated water bath at a temperature of about 40 to 50° C. The vial may be wrapped, such as with paraffin paper to prevent water from entering the vial.

For viscous or solid samples of oil, such as ATB, the vial of oil may be placed on a hot plate at a temperature of from about 120 to 140° C. and stirred, such as with a magnetic stir bar, for about 15 to 20 minutes.

The FTIR analysis was performed using an Alpha Q410 spectrometer, available from Spectro Scientific, equipped with a flip top cell.

A background IR spectrum was taken by placing an empty flip top cell in the FTIR spectrometer and taking an IR spectrum.

An IR spectrum of the oil sample was taken by placing 1 to 2 droplets of the oil onto the flip top cell, loading the flip top cell into the FTIR spectrometer, and taking an IR spectrum of the oil sample.

The flip top cell was then cleaned using Kimtex Wipes, available from Kimberly-Clark. If heavy cleaning is required, a solvent may be used, such as toluene.

Another background IR spectrum was taken by placing the empty, cleaned flip top cell in the FTIR spectrometer and taking an IR spectrum.

One to two droplets of the neutralized sample were placed onto the flip top cell. The flip top cell was allowed to cool for 5 to 10 minutes prior to placing the flip top cell into the FTIR spectrometer and taking an IR spectrum of the neutralized sample. If residual peaks are still present at around a wavelength of 1700 $cm^{-1}$, more KOH may be added to the sample, which may then be stirred, heated, and re-analyzed in the FTIR spectrometer.

Both the oil sample and the neutralized sample were heated and then allowed to cool prior to being placed in the FTIR spectrometer.

In a software application, such as a laboratory information management system, both the IR spectrum of the oil sample 10 and the IR spectrum of the neutralized spectrum 12 were opened in a combined graph 14, as shown in the FIGURE. FIGURE plots absorbance versus wavenumber for both the oil sample and the neutralized sample. The shape of the IR spectrum associated with naphthenic acid may be different for different cuts of crude oil and fractions due to inter and intra-molecular interactions. The IR spectrum of the neutralized spectrum 12 was subtracted from the IR spectrum of the oil sample 10 to determine a modified TAN-IR. The area under the curve resulting from subtraction of the IR spectrum of the neutralized spectrum 12 from the IR spectrum of the oil sample 10 is associated with the concentration of naphthenic acid in the oil sample that was neutralized in the neutralized sample.

While various embodiments have been shown and described, modifications thereof can be made by one skilled in the art without departing from the spirit and teachings of the disclosure. The embodiments described herein are exemplary only, and are not intended to be limiting. Many variations and modifications of the subject matter disclosed herein are possible and are within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.).

What is claimed is:

1. A method comprising:
   obtaining a first sample and a second sample of a crude oil or crude oil fraction that contains naphthenic acid;
   determining an IR spectrum of the first sample;
   contacting the second sample with a metallic hydroxide to form a neutralized sample, wherein the metallic hydroxide comprises magnesium hydroxide, sodium hydroxide, or potassium hydroxide;
   determining an IR spectrum of the neutralized sample, wherein the first sample, the neutralized sample, or both, are subjected to sonication prior to determining their IR spectrums;
   subtracting the IR spectrum of the neutralized sample from the IR spectrum of the first sample to obtain a modified TAN-IR spectrum; and
   using the modified TAN-IR spectrum to determine a formulation of a blend of the crude oil or crude oil fraction with additional crude oil or crude oil fraction, wherein the blend has a modified TAN-IR spectrum that is at or below a predetermined level.

2. The method of claim 1, further comprising blending the crude oil or crude oil fraction with additional crude oil or crude oil fraction to form a blend having a modified TAN-IR at or below a predetermined level.

3. The method of claim 2, further comprising feeding the blend to a distillation unit.

4. The method of claim 3, wherein the distillation unit is an atmospheric or vacuum distillation unit.

5. The method of claim 1, further comprising feeding the crude oil or crude oil fraction to a distillation unit.

6. The method of claim 5, wherein the distillation unit is an atmospheric or vacuum distillation unit.

7. The method of claim 1, wherein the second sample is contacted with an amount of the metallic hydroxide sufficient to neutralize all naphthenic acid in the crude oil or crude oil fraction.

8. The method of claim 1, wherein each IR spectrum is taken within a wavelength range of from about 1,500 to about 2,500 cm$^{-1}$.

9. The method of claim 1, further comprising evaluating a risk of corrosion in processing equipment in contact with the crude oil or crude oil fraction using the modified TAN-IR and a corrosion risk matrix by calculating an estimation of a corrosion rate.

10. The method of claim 1, wherein the determination of the IR spectra and the determination of the modified TAN-IR spectrum is automated.

11. The method of claim 10, further comprising using the determined modified TAN-IR spectrum in real-time, to determine the formulation of the blend of the crude oil or crude oil fraction with additional crude oil or crude oil fraction.

12. The method of claim 10, further comprising using the determined modified TAN-IR spectrum, in real-time, to determine a naphthenic concentration in the crude oil or crude oil fraction.

13. The method of claim 10, further comprising using the determined modified TAN-IR to determine adjustments to a formulation of a blend when the modified TAN-IR for the blend is above a predetermined level, wherein the blend comprises the crude oil or crude oil fraction and additional crude oil or crude oil fraction.

14. The method of claim 13, wherein the modified TAN-IR and the adjustments to the formulation of the blend are determined while the blend is being fed to a distillation unit.

15. The method of claim 14, further comprising adjusting the formulation of the blend to provide the blend with a modified TAN-IR that is at or below the predetermined level.

16. The method of claim 15, wherein the formulation of the blend is adjusted while the blend is continuing to be fed to the distillation unit.

17. A method comprising:
    determining a modified TAN-IR spectrum by subtracting an IR spectrum of a neutralized sample from an IR spectrum of a first sample, wherein the first sample comprises a portion of a crude oil or crude oil fraction that contains naphthenic acid, and wherein the neutralized sample comprises a portion of the crude oil or crude oil fraction after contact with a metallic hydroxide, wherein the metallic hydroxide comprises magnesium hydroxide, sodium hydroxide, or potassium hydroxide wherein the first sample, the neutralized sample, or both, are subjected to sonication prior to determining their IR spectrums; and
    using the modified TAN-IR spectrum to determine a formulation of a blend of the crude oil or crude oil fraction with additional crude oil or crude oil fraction, wherein the blend has a modified TAN-IR spectrum that is at or below a predetermined level.

18. A method comprising:
    obtaining a sample of a crude oil or crude oil fraction that contains naphthenic acid;
    determining an IR spectrum of the sample;
    contacting the sample with a metallic hydroxide to form a neutralized sample, wherein the metallic hydroxide comprises magnesium hydroxide, sodium hydroxide, or potassium hydroxide;
    determining an IR spectrum of the neutralized sample; and
    subtracting the IR spectrum of the neutralized sample from the IR spectrum of the sample to determine a modified TAN-IR spectrum, wherein the sample, the neutralized sample, or both, are subjected to sonication prior to determining their IR spectrums; and
    using the modified TAN-IR spectrum to determine a formulation of a blend of the crude oil or crude oil fraction with additional crude oil or crude oil fraction, wherein the blend has a modified TAN-IR spectrum that is at or below a predetermined level.

* * * * *